United States Patent [19]

Klaus et al.

[11] Patent Number: 4,678,793

[45] Date of Patent: Jul. 7, 1987

[54] HETEROCYCLIC COMPOUNDS

[75] Inventors: Michael Klaus, Weil am Rhein, Fed. Rep. of Germany; Peter Loeliger, Muttenz, Switzerland

[73] Assignee: Hoffmann-La Roche Inc., Nutley, N.J.

[21] Appl. No.: 718,674

[22] Filed: Apr. 1, 1985

Related U.S. Application Data

[62] Division of Ser. No. 491,618, May 5, 1983.

[51] Int. Cl.$^4$ ..................... A61K 31/47; C07D 215/14
[52] U.S. Cl. .................................. 514/311; 546/166; 549/23; 549/398
[58] Field of Search ................. 546/165, 166; 514/311

[56] References Cited

U.S. PATENT DOCUMENTS 4,396,553 8/1983 Klaus ............................. 260/456 NS
4,456,618 6/1984 Dawson et al. .................. 549/57 X

*Primary Examiner*—Richard L. Raymond
*Attorney, Agent, or Firm*—Jon S. Saxe; George M. Gould; William H. Epstein

[57] ABSTRACT

Novel p-[2(4,4-dimethyl-6-heterophenyl)substituted phenyl derivatives and salts thereof which are useful for combatting neoplasms and dermatoses including oral and topical compositions containing said derivatives which are suitable for such uses.

17 Claims, No Drawings

HETEROCYCLIC COMPOUNDS

This is a division of application Ser. No. 06/491,618 filed May 5, 1983.

SUMMARY OF INVENTION

The present invention is directed to novel heterocyclic compounds of the formula:

[Structure I: chroman-like bicyclic system with $H_3C$, $CH_3$ substituents at 4-position, X in ring, connected via $C(CH_3)=CH-$ to phenyl-$R^1$]

wherein
X is $$-O-, -S-, -\underset{\underset{O}{\|}}{S}-, -SO_2- \text{ or } -\underset{\underset{R^2}{|}}{N}-;$$

$R^1$ is methyl, $$-\underset{\underset{R^3}{|}}{C}H-OR^4 \text{ or } -\underset{\underset{O}{\|}}{C}-R^5;$$

$R^2$ is hydrogen or loweralkyl;
$R^3$ is hydrogen or methyl; $R^4$ is hydrogen, loweralkyl or alkanoyl; $R^5$ is hydrogen, lower-alkyl, amino, lower-alkylamino, di(lower-alkyl)amino or $OR^6$; and
$R^6$ is hydrogen or lower-alkyl;
as well as salts of these compounds which are useful for combatting acne and other dermatoses as well as neoplasmas.

The invention is also directed to pharmaceutical preparations containing the compounds of formula I or their salts.

DETAILED DESCRIPTION

The term "lower" used herein denotes groups containing from 1 to 6 carbon atoms. Preferred lower groups contain 1–4 carbon atoms such as methyl, ethyl, n-butyl, t-butyl.

Alkyl groups can be branched or unbranched such as, for example, methyl, ethyl, isopropyl or 2-methyl-propyl.

Alkanoyl groups are derived from lower alkanoyl acids containing from 2 to 6 carbon atoms, for example, from acetic acid, propionic acid or pivalic acid as well as from higher carboxylic acids containing from 7 to 20 carbon atoms such as palmitic acid or stearic acid. Preferred alkanoyl groups are lower alkanoyl groups.

A preferred group of compounds of formula I comprises those in which $R^1$ is carboxyl, lower-alkoxycarbonyl, carbamoyl, monoalkylcarbamoyl or dialkylcarbamoyl.

Among the compounds of formula I are those compounds having the formula:

I-A [chroman with O]
I-B [thiochroman with S]
I-C [thiochroman S-oxide]
I-D [thiochroman S,S-dioxide]
and
I-E [tetrahydroquinoline with $NR^2$]

wherein $R^1$ and $R^2$ are as above.

In the compound of formula I-E, $R^2$ can be hydrogen or lower alkyl particularly methyl or ethyl.

In the compounds of formulae I-A, I-B, I-C and I-D, $R^1$ is preferably carboxyl; lower alkoxycarbonyl such as methoxycarbonyl, ethoxycarbonyl; carbamoyl; lower alkylcarbamoyl such as methylcarbamoyl, ethylcarbamoyl; and di(loweralkyl)carbamoyl, such as dimethylcarbamoyl, N-methyl-N-ethyl-carbamoyl.

Also preferred are those compounds of formula I-A, I-B, I-C and I-D where $R^1$ is $-CH_2-OR^4$ where $R^4$ can be hydrogen or lower alkyl such as methyl, ethyl, etc. or lower alkanoyl such as acetyl, propionyl, etc.

When X in the compound of formula I is $$-\underset{\underset{R^2}{|}}{N}-,$$

the compounds forms salts with non-toxic, pharmaceutically acceptable acids. Among these acids are included hydrochloric acid, phosphoric acid, nitric acid, p-toluenesulphonic acid, acetic acid, propionic acid, citric acid, tartaric acid, maleic acid, etc. In addition to these acids, any conventional pharmaceutically acceptable, nontoxic inorganic or organic acids can be used to form the salts of these compounds. These salts can be prepared by treating the compound of formula I where X is

with the aforementioned acids by conventional means well known in the art.

Also included in the invention are those salts of compounds of formula I where $R^1$ is —COOH with pharmaceutically acceptable, non-toxic, inorganic or organic bases, e.g. alkali metal salts and alkaline earth metal salts, for example sodium, potassium, magnesium or calcium salts, as well as salts with ammonia or suitable non-toxic amines, such as lower alkyl amines, for example triethylamine, hydroxy-lower alkylamines, for example 2-hydroxyethylamine, bis-(2-hydroxyethyl)amine or tris-(2-hydroxyethyl)amine, cycloalkylamines, for example dicyclohexylamine, or benzylamines, for example N,N'-dibenzyl-ethylenediamine, and dibenzylamine.

The compounds of formula I and their salts can be manufactured in accordance with the invention by reacting a compound of the general formula:

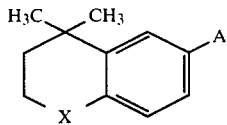

with a compound of the general formula

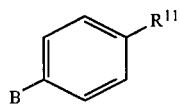

wherein A either is a triarylphosphoniumethyl group of the formula

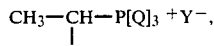

when B is formyl; or A is acetyl when B is a dialkoxyphosphinylmethyl group; $R^{11}$ has any of the values of $R^1$ hereinbefore with the exception of carboxyl and formyl; Q is phenyl; and Y is an anion of an organic acid or an inorganic acid to give a compound of formula I and, if desired, functionally modifying the group denoted by $R^{11}$ and/or oxidizing the sulphur atom in a compound in which X signifies —S— to a sulphoxyl or sulphonyl group.

The chlorine, bromine or hydrosulphate ion is the preferred inorganic acid ion denoted by Y and the tosyloxy ion is the preferred organic acid ion denoted by Y.

The alkoxy groups present in a dialkoxyphosphinylmethyl group denoted by B are particularly lower alkoxy groups containing 1-6 carbon atoms such as methoxy or ethoxy.

The starting materials of formula II can be prepared, insofar as their preparation is not known or described hereinafter, in analogy to known methods or to methods described hereinafter.

The reaction of the compounds of formulae II and III can be carried out according to methods which are known for the Wittig or Horner reaction.

In the case of the Wittig reaction, i.e. using a compound of formula II in which A signifies triarylphosphoniumethyl, the components are reacted with one another in the presence of an acid-binding agent, for example in the presence of a strong base such as, for example, butyl lithium, sodium hydride or the sodium salt of dimethyl sulphoxide, but especially in the presence of an ethylene oxide optionally substituted by lower alkyl such as 1,2-butylene oxide, if desired in a solvent (e.g. an ether such as diethyl ether or tetrahydrofuran or an aromatic hydrocarbon such as benzene) at a temperature between room temperature and the boiling point of the reaction mixture.

In the case of the Horner reaction i.e. using a compound of formula III in which B signifies dialkoxyphosphinylmethyl, the components are reacted together with the aid of a base and preferably in the presence of an inert organic solvent, for example with the aid of sodium hydride in benzene, toluene, dimethylformamide, tetrahydrofuran, dioxan or 1,2-dimethoxyalkane or with the aid of a sodium alcoholate in an alkanol, for example sodium methylate in methanol, at a temperature between 0° C. and the boiling point of the reaction mixture.

As the functional modification of a substituent denoted by $R^1$ or $R^{11}$ in a compound of formula I obtained there comes into consideration, for example the saponification of a carboxylic acid ester or its reduction to the hydroxymethyl group. The hydroxymethyl group can also be oxidized to the formyl group or can be esterified or etherified. Furthermore, a carboxyl group can then be converted into a salt, an ester, an amide or the hydroxymethyl group.

Furthermore, a carboxylic acid ester can be converted into a acetyl group by reaction with a methylmagnesium halide compound at a lower temperature or a carboxyl group can be converted into an acetyl group by reaction with methyl lithium. The acetyl group can be converted by reduction with a complex metal hydride such as, for example, sodium borohydride into the secondary alcohol which can be alkylated or acylated according to known methods.

All of these modification of $R^{11}$ to $R^1$ can be carried out according to known methods.

A carboxylic acid ester of formula I can be hydrolyzed in a known manner, for example by treatment with alkalies, especially by treatment with aqueous-alcoholic sodium or potassium hydroxide in a temperature range from about room temperature to the boiling point of the reaction mixture, and the resulting carboxylic acid can be amidated either via an acid halide, or, as described hereinafter, directly.

A carboxylic acid of formula I can be converted in a known manner, for example by treatment with thionyl chloride, preferably in pyridine, or with phosphorus trichloride in toluene, into the acid chloride which can be converted into an ester by reaction with an alcohol or into a corresponding amide by reaction with an amine such as diethylamine, ethylamine, etc.

A carboxylic acid ester of formula I can be converted directly into the corresponding amide, for example by treatment with lithium amide. The lithium amide is advantageously reacted at room temperature with the ester in question.

A carboxylic acid or a carboxylic acid ester of formula I can be reduced in a known manner to give the corresponding alcohol of formula I for example those compounds of formula I where R¹ is

The reduction is advantageously carried out using a metal hydride or alkyl metal hydride in an inert solvent. Especially suitable hydrides are mixed metal hydrides such as lithium aluminium hydride and bis[methoxyethyleneoxyl]-sodium aluminium hydride. Solvents which can be used are, inter alia, diethyl ether, tetrahydrofuran or dioxan when lithium aluminium hydride is used and diethyl ether, hexane, benzene or toluene when diisobutylaluminium hydride or bis[methoxyethyleneoxy]-sodium aluminium hydride is used.

An alcohol of formula I can be etherified with an alkyl halide (e.g. methyl iodide), for example in the presence of a base, preferably in the presence of sodium hydride, in an organic solvent such as dioxan, tetrahydrofuran, 1,2-dimethoxyethane, dimethylformamide, or in the presence of an alkali metal alcoholate in an alkanol, in a temperature range of from about between 0° to about room temperature.

An alcohol of formula I can also be esterified by treatment with an alkanoyl halide or anhydride, conveniently in the presence of a base, for example in the presence of pyridine or triethylamine, in a temperature range lying between room temperature and the boiling point of the reaction mixture. This esterification produces the compound of formula I where R is —CH-R³OR⁷ and R⁷ is lower alkanoyl such as acetyl.

The carboxylic acids of formula I form salts with bases, especially with alkali metal hydroxides, preferably with sodium hydroxide or potassium hydroxide.

A compound of formula I in which X stands for —S— can be oxidized according to known methods to give a compound of formula I in which X stands for =SO or =SO₂. The oxidation to the sulphoxide group can be carried out using oxidizing agents such as periodates (e.g. sodium periodate) or using organic peracids such as m-chloroperbenzoic acid. When the oxidation is carried out using an organic peracid about 1 equivalent is used in order to obtain a sulphoxide (X=SO), whereas the use of two equivalents of peracid leads to a sulphone (X=SO₂).

The compounds of formula I can be present in the *trans* form or in the *cis* form. In the foregoing process, they result in the majority of cases in the *trans* form. Cis constituents which may be present can be separated in a known manner where desired.

The compounds of formula I and their physiologically compatable salts are pharmacodynamically valuable compounds. They can be used for the topical and systemic therapy of benign and malignant neoplasms and of premalignant lesions as well as for the systemic and topical prophylaxis of these conditions.

They are also suitable for the topical and systemic therapy and prophylaxis of acne, psoriasis and other dermatoses accompanied with an intensified or pathologically altered cornification as well as of inflammatory and allergic dermatological conditions. Further, the compounds of formula I and their physiologically compatible salts can also be used for the control of disorders of the mucous membrane associated with inflammatory or degenerative or metaplastic changes. In the papilloma test (Europ. J. Cancer Vol. 10, pp. 731-737, 1974), the compound prepared in Example 1 (formula I, X=O,R¹=ethoxycarbonyl) exhibits 43% regression of the papilloma with 12.5 mg/kg.

Therefore, the compounds of this invention are useful for combatting both prophylactically or by treatment such disorders as acne, psoriasis and other dermatoses as well as neoplasms of premalignant lesions.

For the treatment and prophylaxis of the aforementioned, compounds of formula I and their physiologically compatible salts can be administered orally, conveniently in a dosage in the case of adults of about 1 to 100 mg per day, preferably from about 5 to 30 mg/day. A possible over-dosage can show itself in the form of a vitamin-A hypervitaminosis and is readily recognized by its symptoms (skin scaling, hair loss).

The dosage can be administered as a single dosage or in several divided dosages. Generally, it is preferred to prepare these dosages as unit oral dose containing from about 0.5 to 100 mg of the active ingredient of formula I or its salts and most preferable between 0.5 to 30 mg of the active ingredient with 0.5 to 20 mg being especially preferred.

The compounds of formula I and their physiologically compatible salts can accordingly be used as medicaments, for example in the form of pharmaceutical preparations.

The pharmaceutical preparations for systemic use can be prepared, for example, by adding a compound of formula I or a physiologically compatible salt thereof as the active ingredient to non-toxic, inert, solid or liquid carriers customary in such preparations.

The pharmaceutical preparations can be administered enterally, parenterally or topically. For enteral administration there are suitable, for example, pharmaceutical preparations in the form of tablets, capsules, dragées, syrups, suspensions, solutions and suppositories. For parenteral administration there are suitable pharmaceutical preparations in the form of infusion or injection solutions.

The dosages in which the preparations are administered can vary according to the type of use, the mode of use and the requirements of the patients.

The preparations can be administered in one or more dosages. A preferred form of administration comprises capsules containing about 0.5-20 mg of active substance.

The pharmaceutical preparations can contain inert as well as pharmacodynamically active additives. Tablets or granulates, for example, can contain a series of binding agents, filling materials, carrier substances or diluents. Liquid preparations can take the form, for example, of a sterile solution which is miscible with water. Capsules can contain, in addition to the active substance, a filling material or thickening agent. Furthermore, flavour-improving additives, substances usually used as preserving, stabilizing, moisture-retaining and emulsifying agents as well as salts for varying the osmotic pressure, buffers and other additives can also be present.

The previously mentioned carrier substances and diluents can be organic or inorganic substances; for example, water, gelatine, lactose, starch, magnesium stearate, talc, gum arabic, polyalkylene glycols and the like. A prerequisite is that all adjuvants used in the manufacture of the pharmaceutical preparations are non-toxic.

For topical administration, the pharmaceutical preparations are conveniently provided in the form of shampoos, salves, tinctures, creams, solutions, lotions, sprays, suspensions and the like. Salves, creams, shampoos and solutions are preferred. These pharmaceutical preparations for topical administration can be manufactured by mixing the compounds provided by the present invention as the active ingredient with non-toxic, inert, solid or liquid carriers which are customary per se in such preparations and which are suitable for topical treatment.

For topical administration there are preferably used from about 0.1 to about 5% by weight, based upon the weight of the topical preparation, of the compound of formula I or its salts. Generally for solutions and shampoos, it is preferable to use the active ingredient in an amount of from about 0.3 to about 2% by weight, based upon the total weight of the composition. In salves and creams, it is generally preferred to incorporate the active ingredient in an amount of from about 0.3% to 2% by weight, based upon total weight of the composition, preferably from about 0.3 to about 0.2%.

If desired, an antioxidant agent (e.g. tocopherol, N-methyl-Γ-tocopheramine, butylated hydroxyanisole or butylated hdyroxytoluene) can be included in the pharmaceutical preparations.

The following Examples illustrate the present invention. The ether used in the Examples was diethyl ether.

EXAMPLE 1

15.9 g of [1-(4,4-dimethyl-6-chromanyl)ethyl]triphenylphosphonium bromide were heated at reflux overnight with 5.5 g of 4-ethoxycarbonylbenzaldehyde in 150 ml of butylene oxide. The mixture was cooled, poured into 500 ml of methanol/water (6:4 parts by volume), extracted three times with hexane, the organic phase was washed with water, dried over sodium sulphate and evaporated. There were obtained 8.1 g of a yellowish oil which was purified by filtration over silica gel [eluting agent: hexane/ether (9:1 parts by volume)]. After recrystallization from hexane/ether, there were obtained 5.7 g of ethyl p-[(E)-2-(4,4-dimethyl-6-chromanyl)propenyl]-benzoate in the form of colorless crystals of melting point 86°–87° C.

The phosphonium salt used as the starting material was prepared as follows:

3.4 g of acetyl chloride were dissolved in 30 ml of nitrobenzene and the solution was treated portionwise at 0°–5° C. with 5.7 g of aluminium trichloride. To this mixture was added dropwise at 0°–5° C. a solution of 6.9 g of 4,4-dimethylchromane in 15 ml of nitrobenzene. After stirring for 1 hour, the mixture was poured into ice/water, extracted with ether, the organic phase was washed with 1N sodium hydroxide solution and a saturated sodium chloride solution, dried over sodium sulphate and evaporated. The residual black oil was distilled in a high vacuum. There were obtained 5.1 g of 4,4-dimethyl-6-acetylchromane in the form of a bluish oil of boiling point 110° C./0.02 mmHg.

20.4 g of 4,4-dimethyl-6-acetylchromane were dissolved in 400 ml of methanol and the solution was treated portionwise with 3.3 g of sodium borohydride while cooling with ice. The mixture was stirred overnight at room temperature, poured into ice/water and extracted with ether. After washing with water, drying the organic phase with sodium sulphate and evaporating the solvent, there were obtained 19.4 g of a brown oil which was purified further by filtration over silica gel (eluting agent: 80% by volume hexane/20% by volume ether). There were obtained 18.2 g of 4,4-dimethyl-6-(1-hydroxyethyl)-chromane in the form of a colorless oil.

6.2 g of 4,4-dimethyl-6-(1-hydroxyethyl)chromane were dissolved in 3 ml of absolute ether and 20 ml of hexane and the solution was treated with 3 drops of pyridine. At a temperature of 0°–5° C. there was slowly added dropwise thereto a solution of 5.4 g of phosphorus tribromide in 20 ml of hexane. The mixture was stirred at 0° C. for a further 3 hours, poured onto ice and extracted with ether. The organic phase was washed with dilute sodium bicarbonate solution and water, dried over sodium sulphate and evaporated. There were obtained 4.5 g of 4,4-dimethyl-6-(1-bromoethyl)chromane in the form of a reddish oil which was converted into the phosphonium bromide without further purification.

4.6 g of 4,4-dimethyl-6-(1-bromoethyl)chromane were dissolved in 40 ml of xylene and the solution was treated with 5.3 g of triphenylphosphine. The mixture was heated to 100° C. overnight, cooled, the precipitated cyrstals were filtered off under suction and washed with hexane. For the further purification, the phosphonium salt was dissolved in methylene chloride and precipitated again by the addition of ethyl acetate. There were obtained 3.5 g of [1-(4,4-dimethyl-6-chromanyl)ethyl]triphenylphosphonium bromide in the form of colorless crystals of melting point 142°–148° C.

EXAMPLE 2

4.0 g of ethyl p-[(E)-2-(4,4-dimethyl-6-chromanyl)-propenyl]benzoate were dissolved in 80 ml of ethanol and the solution obtained was treated with a solution of 5.6 g of potassium hydroxide in 20 ml of water and 20 ml of ethanol. After stirring at 50° C. for 3 hours, the mixture was cooled, poured into ice/water, acidified with 2N sulphuric acid and extracted repeatedly with ethyl acetate. The organic phase was washed with water, dried over sodium sulphate and evaporated. After recrystallization of the residue from methylene chloride/hexane, there was obtained 3.4 g of p-[(E)-2-(3,4-dihydro-4,4-dimethyl-2H-1-benzopyran-6-yl)propenyl]-benzoic acid in the form of colorless crystals of melting point 196°–197° C.

EXAMPLE 3

4.0 g of ethyl p-[(E)-2-(4,4-dimethyl-6-chromanyl)-propenyl]benzoate were dissolved in 50 ml of ether and the solution was treated slowly at 0° C. with 25.2 ml of a diisobutylaluminium hydride solution (20% in toluene). After stirring at 0° C. for 1 hour, 25 ml of methanol/water (1:1) were cautiously added dropwise thereto, the mixture was stirred at room temperature for 30 minutes and the precipitate was filtered off. The filtrate was dried, filtered over a short column of silica gel [eluting agent: hexane/ether (1:1)] and evaporated. After recrystallization from hexane/ether, there was obtained 2.9 g of p-[(E)-2-(3,4-dihydro-4,4-dimethyl-1-benzopyran-6-yl)propenyl]benzyl alcohol in the form of colorless crystals of melting point 80°–81° C.

EXAMPLE 4

105 mg of a 50% dispersion of sodium hydride in mineral oil were washed 3 times with pentane, dried in vacuo and suspended in 10 ml of dimethylformamide.

At 0° C., there was added dropwise thereto a solution of 500 mg of p-[(E)-2-(3,4-dihydro-4,4-dimethyl-1-benzopyran-6-yl)propenyl]benzyl alcohol in 5 ml of dimethylformamide. After 30 minutes, 400 mg of ethyl iodide were added thereto and the mixture was stirred at room temperature for 2 hours. The mixture was then poured into ice/water, extracted with ether, dried and evaporated. Recrystallization of the crude product from hexane gave 150 mg of 6-[(E)-p-(ethoxymethyl)-α-methylstyryl]-4,4-dimethyl-2-H-1-benzopyran of melting point 59°–60° C.

EXAMPLE 5

0.5 g of p-[(E)-2-(3,4-dihydro-4,4-dimethyl-1-benzopyran-6-yl)propenyl]benzyl alcohol was dissolved in 20 ml of methylene chloride and the solution is treated with 10 g of manganese dioxide. After stirring at room temperature for 6 hours, the solid material is filtered off, rinsed well with methylene chloride and the filtrate was evaporated. After recrystallization of the residue from hexane/ether, there are obtained 350 mg of p-[(E)-2-(3,4-dihydro-4,4-dimethyl-2H-1-benzopyran-6-yl)propenyl]benzaldehyde of melting point 102°–104° C.

EXAMPLE 6

0.5 g of p-[(E)-2-(3,4-dihydro-4,4-dimethyl-2H-1-benzopyran-6-yl)propenyl]benzoic acid were dissolved in 10 ml of tetrahydrofuran and the solution was treated with 0.29 g of 1,1'-carbonyldiimidazole. After stirring at room temperature for 2 hours, there was obtained a clear solution into which dry ethylamine was conducted for 1 hour while cooling with ice. The mixture was subsequently poured onto ice, acidified with 2N sulphuric acid, extracted with ethyl acetate, dried and evaporated. The crude product was filtered over a column of silica gel [eluting agent: hexane/ethyl acetate (3:1)] and recrystallized from ethyl acetate/hexane. There was obtained 0.4 g of p-[2-(3,4-dihydro-4,4-dimethyl-2H-1-benzopyran-6-yl)propenyl]-N-ethyl-benzamide of melting point 161°–163° C.

EXAMPLE 7

0.5 g of p-[(E)-2-(3,4-dihydro-4,4-dimethyl-2H-1-benzopyran-6-yl)propenyl]-benzoic acid was dissolved in 10 ml of tetrahydrofuran. While cooling with ice, there are slowly added dropwise thereto 2.3 ml of a 1.6 molar solution of methyl lithium in ether. After stirring at room temperature for 30 minutes, the mixture was poured onto ice, extracted with ether, dried and evaporated. After recrystallization of the residue from hexane/ether, there was obtained 370 mg of 4'-[2-(3,4-dihydro-4,4-dimethyl-2H-1-benzopyran-6-yl)propenyl]acetophenone of melting point 109°–110° C.

EXAMPLE 8

37 g of aluminium chloride were suspended at 0° C. in 200 ml of methylene chloride and the suspension was treated slowly with 22 g of acetyl chloride while stirring vigorously. After 30 minutes, a solution of 49.4 g of 3,4-dihydro-4,4-dimethyl 2H-1-benzothiopyran in 150 ml of methylene chloride was added dropwise thereto. After stirring at 0° C. for 1 hour, the mixture was poured into ice/water and extracted with methylene chloride. The organic phase was washed neutral with 1N sodium hydroxide solution and water, dried and evaporated. The oily crude product was filtered over a short column of silica gel [eluting agent: hexane/ether (9:1)]. There were obtained 51.5 g of 3,4-dihydro-4,4-dimethyl-2H-1-benzothiopyran-6-yl methyl ketone in the form of a colorless oil which solidifies upon standing in a refrigerator.

EXAMPLE 9

2.6 g of a 50% dispersion of sodium hydride in mineral oil were washed 3 times with pentane, dried in vacuo and suspended in 100 ml of dimethylformamide. At room temperature there was added dropwise thereto a solution of 16.4 g of diethyl 4-ethoxycarbonyl-benzylphosphonate in 100 ml of dimethylformamide. After stirring at room temperature for 30 minutes, there was added dropwise thereto a solution of 10 g of 3,4-dihydro-4,4-dimethyl-2H-1-benzothiopyran-6-yl methyl ketone in 80 ml of dimethylformamide and the mixture was subsequently heated to 70° C. for 2.5 hours. After cooling, the mixture was poured into ice/water, acidified with 2N hydrochloric acid and extracted with ether. The organic phase was washed repeatedly with water, dried and evaporated. There was obtained a yellow oil which, after chromatography on silica gel [eluting agent: hexane/ethyl acetate (4:1)] and crystallization from hexane, gave 9.8 g of ethyl p-[(E)-2-(3,4-dihydro-4,4-dimethyl-2H-1-benzothiopyran-6-yl)propenyl]benzoate in the form of slightly yellowish crystals of melting point 91°–92° C.

EXAMPLE 10

4.0 g of ethyl p-[(E)-2-(3,4-dihydro-4,4-dimethyl-2H-1-benzothiopyran-6-yl)propenyl]benzoate were dissolved in 100 ml of chloroform. While stirring there was slowly added dropwise thereto at 0°–5° C. a solution of 5 mg of m-chloroperbenzoic acid (about 90%) in 100 ml of chloroform and the mixture was stirred at 0°–5° C. overnight. The mixture was diluted with chloroform, washed twice with dilute sodium carbonate solution and water, dreid and evaporated. After filtration of the crude product over silica gel [eluting agent: hexane/ethyl acetate (3:1)] and crystallization from hexane/ethyl acetate, there were obtained 2.3 g of ethyl p-[(E)-2-(3',4'-dihydro-4',4'-dimethyl-2'H-1'-benzothiopyran-6'-yl)propenyl]benzoate 1',1'-dioxide in the form of colorless cyrstals of melting point 142°–144° C.

EXAMPLE 11

In analogy to Example 10, from 4.0 g of ethyl p-[(E)-2-(3,4-dihydro-4,4-dimethyl-2H-benzothiopyran-6-yl)propenyl]benzoate and 2.5 g of m-chloroperbenzoic acid there were obtained, after filtration over silica gel [eluting agent: hexane/ethyl acetate (1:2)] and crystallization from hexane/ethyl acetate, 2.8 g of ethyl p[(E)-2-(3',4'-dihydro-4',4'-dimethyl-2'H-1'-benzothiopyran-6'-yl)propenyl]benzoate 1'-oxide of melting point 97°–99° C.

EXAMPLE 12

By the procedure of Example 1, from [1-(4,4-dimethyl-6-thiochromanyl)ethyl]triphenylphosphonium bromide and 4-ethoxycarbonylbenzaldehyde there is obtained ethyl p-[(E)-2-(4,4-dimethyl-6-thiochromanyl)-propenyl]benzoate.

The phosphonium salt used as the starting material can be prepared starting from 4,4-dimethylthiochromane by the method described in paragraphs 2 through 4 of Example 1.

EXAMPLE 13

By the procedure of Example 1, from [1-(4,4-dimethyl-1,2,3,4-tetrahydro-6-quinolinyl)ethyl]triphenylphosphonium bromide and 4-ethoxycarbonylbenzaldehyde there is obtained ethyl p-[(E)-2-(4,4-dimethyl-1,2,3,4-tetrahydro-6-quinolinyl)propenyl]benzoate.

The phosphonium salt used as the starting material can be prepared starting from 4,4-dimethyl-1,2,3,4-tetrahydroquinoline in analogy to the method described in paragraphs 2 through 4 of Example 1.

EXAMPLE 14

By the procedure of Example 1, from [1-(1,4,4-trimethyl-1,2,3,4-tetrahydro-6-quinolinyl)ethyl]triphenylphosphonium bromide and 4-ethoxycarbonylbenzaldehyde there is obtained ethyl p-[(E)-2-(1,4,4-trimethyl-1,2,3,4-tetrahydro-6-quinolinyl)propenyl]benzoate.

The phosphonium salt used as the starting material can be prepared starting from 1,4,4-trimethylquinoline in analogy to the method described in paragraphs 2 through 4 of Example 1.

EXAMPLE 15

By treating p-[(E)-2-(4,4-dimethyl-6-chromanyl)propenyl]benzyl alcohol with acetyl chloride and pyridine there is obtained p-[(E)-2-(4,4-dimethyl-6-chromanyl)propenyl]benzyl acetate.

EXAMPLE 16

74.5 mg of sodium hydride (50% in mineral oil) was washed with absolute pentane, dried under a water-jet vacuum and suspended in 5 ml of absolute dimethylformamide. A solution of 465 mg of diethyl 4-ethoxycarbonyl-benzylphosphonate at 5 ml of absolute dimethylformamide was added dropwise thereto at room temperature. After stirring for 10 minutes, there was added thereto a solution of 410 mg of 6-acetyl-1,2,3,4-tetrahydro-1,4,4-trimethyl-quinoline in 5 ml of dimethylformamide and the resulting mixture was heated to 70° C. for 1 hour and subsequently to 90° C. for a further 2 hours. After cooling, the mixture was poured on to ice and extracted repeatedly with ether. The ether extracts were washed with water, dried over sodium sulphate and evaporated. After chromatography of the crude product on silica gel [eluting agent: hexane/ether (4:1)], there was obtained ethyl p-[(E)-2-(1,2,3,4-tetrahydro-1,4,4-trimethyl-6-quinolinyl)propenyl]benzoate in the form of pale yellow crystals of melting point 100°-101° C.

The 6-acetyl-1,2,3,4-tetrahydro-1,4,4-trimethyl-quinoline used as the starting material was prepared as follows:

21.5 g of 3,4-dihydro-1,4,4-trimethyl-2(1H)-quinolinone were dissolved in 43 g of carbon disulphide and the solution was treated with 85 g of aluminum chloride. 17.8 g of acetyl chloride were slowly added dropwise thereto while cooling with ice and stirring vigorously. The mixture was subsequently heated at reflux for 1.5 hours, cooled and treated cautiously with ice-water. The resulting mixture was extracted three times with ethyl acetate and the ethyl acetate extracts were washed with water, dried and evaporated. The thus-obtained brownish oil was filtered over silica gel [eluting agent: hexane/ethyl acetate (2:1)] and then recrystallized from hexane/ethyl acetate. There were obtained 19.5 g of 6-acetyl-3,4-dihydro-1,4,4-trimethyl-2(1H)-quinolinone in the form of colourless crystals of melting point 75°-77° C.

5.0 g of 6-acetyl-3,4-dihydro-1,4,4-trimethyl-2(1H)-quinolinone were dissolved in 200 ml of benzene and, after the addition of 2.1 g of ethylene glycol and a few crystals of p-toluenesulphonic acid, the mixture was boiled under a water separator for 5 hours. After cooling, the mixture was diluted with ethyl acetate, washed with dilute sodium hydrogen carbonate solution, dried and evaporated. There were obtained 5.6 g of 3,4-dihydro-1,4,4-trimethyl-6-(2-methyl-1,3-dioxolan-2-yl)-2(1H)-quinolinone in the form of a colourless oil which solidified upon standing in a refrigerator; melting point 81°-83° C. This compound was used in the next step without further purification.

0.14 g of lithium aluminium hydride was suspended in 10 ml of absolute ether and treated dropwise at room temperature with a solution of 1.0 g of 3,4-dihydro-1,4,4-trimethyl-6-(2-methyl-1,3-dioxolan-2-yl)-2(1H)-quinolinone in 15 ml of absolute tetrahydrofuran. After stirring at room temperature for 2 hours, ice-water was slowly added dropwise to the mixture while cooling, the resulting mixture was extracted three times with ethyl acetate, the organic phase was washed with water, dried and evaporated. The thus-obtained brownish oil was dissolved in 10 ml of tetrahydrofuran and, after the addition of 5 ml of 1N sulphuric acid, the mixture was stirred at room temperature for 1.5 hours. The mixture was then poured into ice-water, made alkaline by the addition of 1N sodium hydroxide solution and extracted with ethyl acetate. The organic phase was washed with water, dried and evaporated. The crude product obtained was purified further by chromatography on silica gel [eluting agent: hexane/ethyl acetate (9:1)] and are 460 mg of 6-acetyl-1,2,3,4-tetrahydro-1,4,4-trimethyl-quinoline in the form of a greenish viscous oil.

In the following Examples, the compound is ethyl p-[(E)-2-(4,4-dimethyl-6-chromanyl)propenyl]benzoate.

EXAMPLE A

Capsules for oral administration can have the following composition:

|  | Per capsule |
| --- | --- |
| Compound | 0.5 mg |
| Wax mixture | 50.5 mg |
| Vegetable oil | 98.9 mg |
| Trisodium salt of ethylenediamine-tetraacetic acid | 0.5 mg |

EXAMPLE B

A salve can have the following composition:

|  | Per capsule |
| --- | --- |
| Compound | 0.2 g |
| Cetyl alcohol | 2.7 g |
| Lanolin | 6.0 g |
| Vaseline | 15.0 g |
| Distilled water q.s. ad | 100.0 g |

We claimed:
1. A compound of the formula:

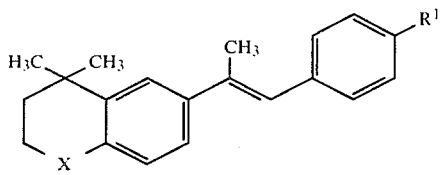

wherein X is

$R^1$ is methyl,

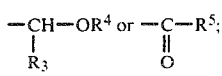

$R^2$ is hydrogen or lower alkyl; $R^3$ is hydrogen or methyl; $R^4$ is hydrogen, lower alkyl or alkanoyl; $R^5$ is hydrogen, lower alkyl, amino, lower alkylamino, di(lower alkyl)-amino or $OR^6$; and $R^6$ is hydrogen or lower alkyl;

or pharmaceutically acceptable salts thereof.

2. The compound of claim 1 wherein $R^1$ is carboxyl, lower alkoxycarbonyl, carbamoyl, lower alkylcarbamoyl or di(lower-alkyl)carbamoyl.

3. The compound of claim 2 wherein $R^1$ is lower alkoxycarbonyl.

4. The compound of claim 3 wherein said compound is ethyl p-[(E)-2-(4,4-dimethyl-1,2,3,4-tetrahydro-6-quinolinyl)propenyl]benzoate.

5. The compound of claim 3 wherein said compound is ethyl p-[(E)-2-(1,4,4-trimethyl-1,2,3,4-tetrahydro-6-quinolinyl)propenyl]benzoate.

6. A method for combatting acne or psoriasis comprising administering to a patient an effective amount of a compound of the formula

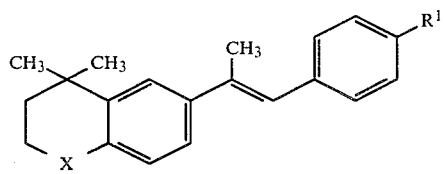

wherein X is

$R^1$ is methyl,

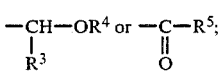

$R^2$ is hydrogen or lower alkyl; $R^3$ is hydrogen or methyl; $R^4$ is hydrogen, lower alkyl or alkanoyl; $R^5$ is hydrogen, lower alkyl, amino, lower alkyl-amino, di(lower-alkyl)amino or $OR^6$; and $R^6$ is hydrogen or lower alkyl;

or pharmaceutically acceptable salts thereof.

7. The method of claim 6 wherein said compound is administered orally.

8. The method of claim 6 wherein said amount is from 1 to 100 mg per day.

9. The method of claim 6 wherein said compound is administered topically.

10. The method of claim 9 wherein said preparation contains said compound in an amount of from 0.1 to 5% based upon the weight of said composition.

11. A method for combatting neoplasms comprising administering to a patient in an effective amount of a compound of the formula:

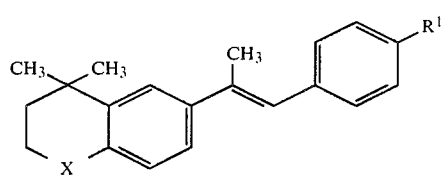

wherein X is

$R^1$ is methyl,

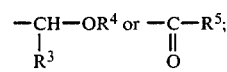

$R^2$ is hydrogen or lower alkyl; $R^3$ is hydrogen or methyl; $R^4$ is hydrogen, lower alkyl or lower alkanoyl; $R^5$ is hydrogen, lower alkyl, amino, alkylamino, di(lower-alkyl)amino or $OR^6$; and $R^6$ is hydrogen or lower alkyl;

or pharmaceutically acceptable salts thereof.

12. The method of claim 11 wherein said amoutn is from 0.5 to 100 mg per day administered orally.

13. The method of claim 12 wherein said compound is administered orally.

14. A composition in oral unit dosage form comprising from about 0.5 to about 100 mg of a compound of the formula:

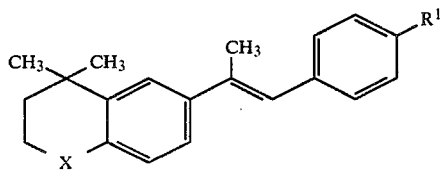

wherein X is

$R^1$ is methyl,

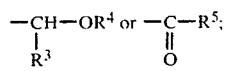

$R^2$ is hydrogen or lower alkyl; $R^3$ is hydrogen or methyl; $R^4$ is hydrogen, lower alkyl or alkanoyl; $R^5$ is hydrogen, lower alkyl, amino, lower alkylamino, di(lower-alkyl)amino or $OR^6$; and $R^6$ is hydrogen or lower alkyl;

and an inert pharmaceutically acceptable carrier.

15. The composition of claim 14 wherein said compound is present in an amount of from 5 to 30 mg.

16. A composition for topical administration comprising a therapeutically inert pharmaceutically acceptable carrier and from about 0.1 to 5% by weight based upon the weight of the composition of a compound of the formula:

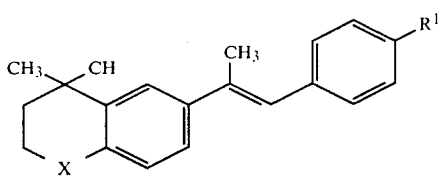

wherein X is

$R^1$ is methyl,

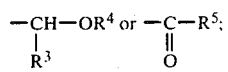

$R^2$ is hydrogen or lower alkyl; $R^3$ is hydrogen or methyl; $R^4$ is hydrogen, lower alkyl or alkanoyl; $R^5$ is hydrogen, lower alkyl, amino, lower alkylamino, di(lower-alkyl)amino or $OR^6$; and $R^6$ is hydrogen or lower alkyl;

or pharmaceutically acceptable salts thereof.

17. The compound of claim 14 wherein said composition is in the form of a shampoo, cream, lotion or salve.

* * * * *

UNITED STATES PATENT AND TRADEMARK OFFICE
CERTIFICATE OF CORRECTION

PATENT NO. : 4,678,793
DATED : July 7, 1987
INVENTOR(S) : Michael Klaus, Germany, Peter Loeliger, Switzerland It is certified that error appears in the above-identified patent and that said Letters Patent are hereby corrected as shown below:

Title page:

[30] Foreign Application Priority Data

May 12, 1982 [CH] Switzerland....................2956/82

Signed and Sealed this

Third Day of November, 1987

Attest:

DONALD J. QUIGG

Attesting Officer

Commissioner of Patents and Trademarks